US 6,555,065 B1

(12) United States Patent
Melet

(10) Patent No.: US 6,555,065 B1
(45) Date of Patent: Apr. 29, 2003

(54) AUTOMATIC HEMATOLOGIC COUNTING AND ANALYSING DEVICE

(76) Inventor: Francois Melet, 9, Chaussée Jules César, OSNY, 95528 Cergy Pontoise Cedex (FR)

( * ) Notice: Subject to any disclaimer, the term of this patent is extended or adjusted under 35 U.S.C. 154(b) by 0 days.

(21) Appl. No.: 09/554,748

(22) PCT Filed: Nov. 16, 1998

(86) PCT No.: PCT/FR98/02440

§ 371 (c)(1),
(2), (4) Date: May 18, 2000

(87) PCT Pub. No.: WO99/26056

PCT Pub. Date: May 27, 1999

(30) Foreign Application Priority Data

Nov. 19, 1997 (FR) .......................................... 97 14520

(51) Int. Cl.[7] .............................................. G01N 33/48
(52) U.S. Cl. .............................. 422/73; 436/10; 436/63
(58) Field of Search ........................... 422/73, 99, 100, 422/103; 436/10, 63

(56) References Cited

U.S. PATENT DOCUMENTS

| | | | |
|---|---|---|---|
| 4,729,876 A | | 3/1988 | Hennessy et al. ............ 422/103 |
| 5,266,269 A | * | 11/1993 | Niiyama et al. .............. 422/73 |
| 5,380,491 A | * | 1/1995 | Carver, Jr. et al. ............ 422/73 |

FOREIGN PATENT DOCUMENTS

| | | | |
|---|---|---|---|
| EP | 335789 | * | 10/1989 |
| EP | 351256 | * | 1/1990 |
| EP | 357466 | * | 3/1990 |
| EP | 0 508 495 A1 | | 10/1992 |
| EP | 510722 | * | 10/1992 |
| WO | WO 95/18962 | | 7/1995 |

* cited by examiner

Primary Examiner—Maureen M. Wallenhorst
(74) Attorney, Agent, or Firm—VanOphem & VanOphem, P.C.

(57) ABSTRACT

A compact apparatus for automatically analyzing a blood sample having a pumping assembly, a dilution assembly and a measuring assembly. The pumping assembly includes pumps for air, lysis and diluent. The dilution assembly includes a sampling needle, and containers for waste, white corpuscle dilution, and red corpuscle dilution. The measuring assembly includes a measuring chamber, and a device for counting platelets, red corpuscles, white corpuscles and hemoglobin in the blood sample. Both red and white corpuscles are counted in the same measuring chamber. A plurality of pipes establish fluid communication between the elements of the apparatus. A plurality of electro-valves are adapted to automatically open and close the pipes thereby regulating fluid flow between the pumping assembly, the dilution assembly and the measuring assembly. One of the electro-valves is adapted to shutoff a diluent source and substitute water therefor, whereby the apparatus is rinsed with the water to avoid crystalization.

18 Claims, 1 Drawing Sheet

AUTOMATIC HEMATOLOGIC COUNTING AND ANALYSING DEVICE

CROSS REFERENCE TO RELATED APPLICATIONS

This application claims the benefit of French Patent Application No. 97 14520 filed Nov. 19, 1997 and International Application No. PCT/FR98/02440 filed Nov. 16, 1998.

BACKGROUND OF THE INVENTION

1. Field of the Invention

The present invention relates to an automatic hematologic counting and analyzing device. More precisely it relates to a device making it possible, in particular, to automatically measure platelets, red corpuscles, white corpuscles and hemoglobin in blood.

2. Description Of The Related Art

French Patent No. 2,629,208 describes an automatic hematologic analyzer. This device, even though already simplified, remains relatively complex. This complexity means that such a device is necessarily bulky and furthermore its manufacturing cost is high. The purpose of the present invention is to overcome the known difficulties of the prior art by reducing the number of useful parts in the device thereby minimizing the volume of the device.

BRIEF SUMMARY OF THE INVENTION

The device of the present invention is of very compact size. Its prime feature is its compactness considering its high performance in matters of analysis, storage and the processing of hematologic measurements. In order to realize such a concept, each assembly and subassembly was studied at length to optimize the mechanical principles of dilution and acquisition of this analyzer. The operating principle of the device of the present invention is described in detail in French Patent No. 2,629,208, EP 0 508 495 and EP 0 335 789 whose descriptions are incorporated herein by reference.

The present invention relates to an automatic hematologic counting and analyzing device that is arranged in three assemblies: a pumping assembly including an air pump driven by a first motor and three pumps for lysis, diluent and sampling, respectively, actuated by a second motor; a diluting assembly including three containers for waste material, first dilution for white corpuscles and second dilution for red corpuscles, respectively; and a measuring assembly including a measuring chamber.

The careful grouping of the various elements constituting the device makes it possible to minimize the volume necessary.

The measuring unit of the device is a single measuring chamber that makes it possible to carry out the counting of platelets, red corpuscles and white corpuscles. By using only one measuring chamber, the cost of the device is lowered and the volume of the device is reduced.

The device has a set of valves that advantageously includes a valve that permits the use of water instead of an isotonic diluent. Rinsing with distilled water makes it possible to put the device on standby without risking crystallization due to salts present in the diluent.

The characteristics and advantages of the invention will become more apparent from a reading of the following description given by way of non-limiting example with reference to the accompanying drawing.

Figure 1:
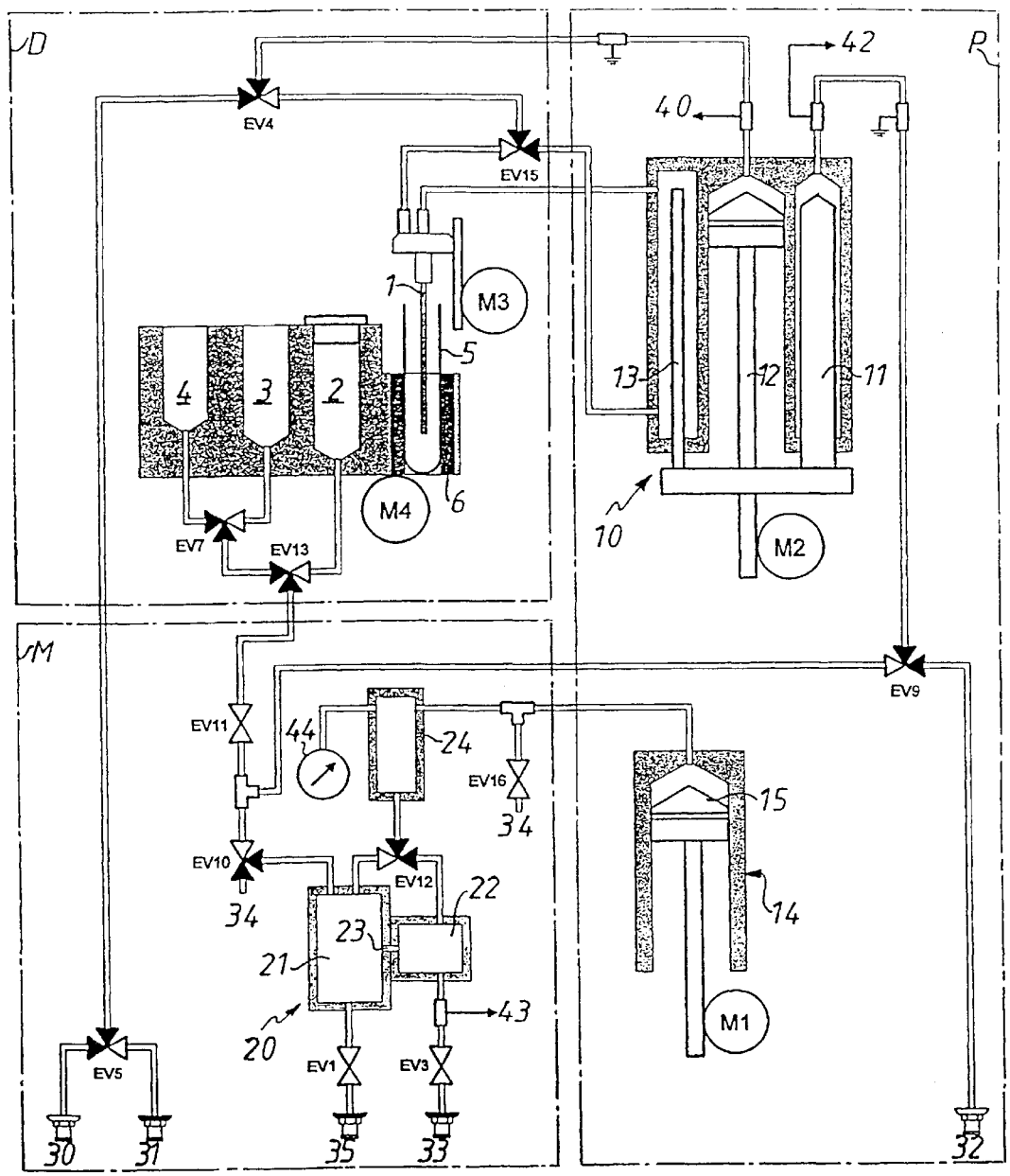
FIG. 1 is a diagrammatic view illustrating the fluid connections of the device of the present invention.

According to the embodiment shown, the device of the present invention makes it possible to carry out hematologic measurements.

DETAILED DESCRIPTION OF THE PREFERRED EMBODIMENT

The device of the present invention includes a pump assembly P, a dilution assembly D, and a measuring assembly M. A set of electro-valves and pipes preferably interconnect the assemblies. The device also includes an electronic assembly for amplification and acquisition of electrical pulses and various peripherals for data acquisition (such as a bar code reader, external PC keyboard, etc.), display, printing and transmission of results.

The dilution assembly D includes a blood sampling device that has a sampling needle 1 driven by a raising and lowering motor M3, and a set of containers for waste material 2, white corpuscle dilution 3 and red corpuscle dilution 4, driven in translation by a motor M4. A sampling tube 5 is disposed in a tube holder 6.

The pump assembly P has a pump 10 with three pistons 11, 12 and 13 that are driven by a motor M2. The lysis piston 11, preferably of average size, connected to an electro-valve EV9, ensures the distribution of a lysis reagent that is useful in the measurement of leukocytes. The diluent piston 12 connected to an electro-valve EV4 ensures the distribution of the diluent necessary for the dilution of the blood. The piston 13 is a micro-piston that is directly connected to the sampling needle 1 and that is used for sampling blood by volume difference. An air pump 14 having a piston 15 is driven by a motor M1 and actuates the measuring assembly M.

The measuring assembly M includes an expansion vessel 24 connected to the air pump 14, a measuring chamber 20 having a main chamber 21 connected to an electro-valve EV1, and a lateral chamber 22 connected to an electro-valve EV3. A micro-orifice 23, also called a counting orifice, is disposed between the main chamber 21 and the lateral chamber 22. A set of pipes and a set of electro-valves ensure interconnection of the various parts.

The pipes are fed by sources of diluent 30 (preferably isotonic diluent), water 31 (preferably distilled water), lysis 32, transflux 33 and air 34. An outlet 35 is provided for drainage. Devices monitor the respective levels of the diluent at 40, the lysis at 42 and the transflux at 43. The monitoring of air pressure is carried out by 2 a device 44.

The electro-valves form a communication logic between the different parts of the device. A first sub-set of electro-valves is used for switching liquids; thus the electro-valve EV1 is used as a general drainage valve, the electro-valve EV3 is used for priming transflux in the lateral chamber 22, EV4 is an electro-valve for the intake and distribution of diluent 30 or water 31, EV5 is an electro-valve that is used for selecting the diluent 30 or the water 31, and EV11 is an electro-valve that manages all of the transfer from the containers 2, 3 and 4 of the dilution assembly D. The electro-valve EV9 is used for the distribution of lysis 32, and EV13 and EV7 are electro-valves that are used for selecting the containers 2, 3 and 4 of the dilution assembly D to be transferred. EV15 is an electro-valve that distributes diluent through the sampling needle 1 for rinsing the inside of the needle, or distributes diluent on the outside of the sampling needle 1 for the first part of the dilution or for rinsing the outside of the needle.

A second sub-set of electro-valves is used for controlling the air circuits. EV12 is an electro-valve that is used for selecting the intake of the air pump 14, and EV16 is an electro-valve that connects the air pump 14 with the atmosphere. EV10 is an electro-valve that permits the intake of air and the transfer of liquid. This electro-valve is used for the counting phase.

An interesting and fundamental feature of the concept of the device of the present invention is the ability of the dilution assembly D to replace the diluent 30 (9 per 1000) with the water 31 by means of the electro-valve EV5. In effect, the water 31 allows rinsing for the purpose of putting the device on standby without risk of crystallization due to salts present in the diluent.

An apparatus based on the arrangement described hereinabove can be produced in a volume having a 33 cm height, 21 cm width and 24 cm depth, including all peripheral equipment.

The functioning of the device will now be described in detail. It is assumed that the priming cycles have been carried out and the reagents are correctly primed. The sampling tube 5 containing blood to be analyzed is inserted in the tube holder 6 and the set of containers 2, 3, and 4 is pushed into the apparatus. Under the action of the motor M4, the sampling tube 5 is positioned under the sampling needle 1. The dilution phase is then carried out. The sampling needle 1 is lowered into the sampling tube 5 due to the action of the motor M3.

Under the action of the motor M2, the desired quantity of blood is drawn up by withdrawing the micro-piston 13. In this way a quantity of diluent 30 proportional to the displacement of the diluent piston 12 is drawn in while the presence of diluent 30 is constantly monitored by the monitoring device 40. The sampling needle 1 is withdrawn from the blood by raising it with the motor M3. A complementary quantity of diluent 30 is then aspirated by the action of the motor M2 while the presence of diluent 30 continues to be monitored by the monitoring device 40. This complementary diluent 30 makes it possible to have the quantity necessary for dilution and rinsing.

The set of containers 2, 3, and 4 is displaced by the motor M4 in order to bring the waste material container 2 of the dilution assembly D under the sampling needle 1. The sampling needle 1 is lowered into the waste material container 2 by the motor M3.

The electro-valves EV4 and EV15 are operated and the motor M3 slowly raises the sampling needle 1. Then, by the action of the motor M2, diluent 30 is pushed in order to rinse the external part of the sampling needle 1.

The electro-valves EV4 and EV15 are turned off and it is verified that the sampling needle 1 is completely raised. The motor M4 displaces the set of containers 2, 3 and 4 and brings the white corpuscle dilution container 3 under the sampling needle 1. The sampling needle 1 is lowered by the action of the motor M3 into the white corpuscle dilution container 3. The electro-valves EV4 and EV15 are operated and the motor M2 is actuated in order to.bring a small quantity of diluent 30 into the white corpuscle dilution container 3.

The electro-valve EV15 is turned off and the motor M2 is actuated in order to bring the quantity of diluent 30 necessary for the correct dilution ratio into the white corpuscle dilution container 3 while ensuring its mixing with all of the blood. The sampling needle 1 is raised and lowered by the motor M3 in order to ensure drop-removal, and the sampling needle 1 is repositioned above the white corpuscle dilution container 3 for aspiration. A sampling is carried out as before but this time with pre-diluted blood, that is to say the blood that is in the white corpuscle dilution container 3. The motor M4 brings the red corpuscle dilution container 4 under the sampling needle 1. The motor M3 lowers the sampling needle 1 into the red corpuscle dilution container 4. The electro-valves EV4 and EV15 are operated and the motor M2 is actuated in order to rinse the external part of the sampling needle 1 with diluent 30. The electro-valves EV4 and EV15 are turned off and the sampling needle 1 is raised by the action of the motor M3 in order to bring it out of the blood. The sampling needle 1 is lowered and raised by the action of the motor M3 in order to ensure drop-removal.

The electro-valves EV10, EV11 and EV12 are operated and the motor M1 is started in order to draw in the liquid from the red corpuscle dilution container 4, which is then transferred into the measuring chamber 20. The pressure is monitored continuously by the monitoring device 44. The electro-valve EV11 is turned off, the electro-valve EV1 is operated and the motor M1 is actuated for draining.

The electro-valve EV1 is turned off and the electro-valve EV16 is operated in order to restore atmospheric pressure in the red corpuscle dilution container 4. The electro-valves EV10, EV11 and EV16 are then turned off.

The dilution of the red corpuscles is then carried out in a similar way to that of the white corpuscles. The sampling needle 1 is then raised.

The counting of the red corpuscles is then carried out. The electro-valves EV10, EV11 and EV12 are operated, and the liquid in the red corpuscles dilution container 4 is aspired and transferred into the measuring chamber 20. The pressure is monitored continuously by the monitoring device 44.

The electro-valves EV10 and EV11 are turned off, the electro-valve EV16 is operated and the motor M1 is actuated in order to return the piston 15 of the air pump 14.

The electro-valves EV12 and EV16 are turned off, the electro-valve EV3 is operated and the motor M1 is actuated in order to prime the transflux 33 in the lateral chamber 22. The presence of the transflux 33 is monitored by the monitoring device 43.

The electro-valve EV3 is turned off and the electro-valve EV16 is operated in order to restore atmospheric pressure.

The electro-valve EV16 is turned off and the motor M1 is actuated in order to decrease pressure in the lateral chamber 22. The pressure is continuously monitored by the monitoring device 44. An electronic counting cycle is then carried out, including controlled programming of probe voltage, acquisition of the white corpuscles of the hemoglobin, and counting the platelets over the programmed duration with a simultaneous monitoring of probe voltage and pressure. The motor M1 is actuated to adjust incorrect pressure levels identified by the monitoring device 44. The red corpuscles are counted over the programmed duration while simultaneously monitoring the voltage of the probe and the pressure.

The electro-valve EV16 is operated in order to restore atmospheric pressure and the motor M1 is actuated in order to take a maximum quantity of air 34. The electro-valve EV16 is turned off, the electro-valves EV10, EV12 and EV1 are operated, and the motor M1 is actuated in order to drive the liquid to the drainage outlet 35. Simultaneously, the motor M2 is actuated in order to aspirate the quantity of diluent 30 necessary for rinsing the measuring chamber 20. The presence of diluent 30 is monitored continuously by the monitoring device 40. The electro-valve EV1 is turned off.

A rinsing cycle is then carried out. The electro-valve EV4 is operated and the motor M2 is actuated in order to put diluent 30 into the red corpuscle dilution container 4. The electro-valves EV10 and EV11 are operated and then the motor M1 is actuated in order to transfer rinsing liquid into the measuring chamber 20. The electro-valve EV11 is turned off, the electro-valve EV1 is operated and the motor M1 is actuated in order to drive the rinsing liquid to the drainage outlet 35.

All of the electro-valves and the motors are then turned off and the white corpuscles are counted. The electro-valve EV9 is operated and the motor M2 is actuated in order to take the programmed quantity of lysis 32 while continuously monitoring the presence of lysis 32 with the monitoring device 42. The electro-valve EV9 is turned off and the electro-valves EV7, EV10, EV11 and EV12 are operated. The motor M2 is actuated in order to drive the lysis 32, and the motor M1 is actuated simultaneously in order to aspirate the liquid which is in the white corpuscle dilution container 3. The electro-valves EV7, EV10 and EV11 are turned off, the electro-valve EV16 is operated and the motor M1 is actuated in order to return the piston 15 of the air pump 14. The white corpuscles are counted in a way similar to that of the red corpuscles.

An electronic counting cycle is carried out including, controlled programming of probe voltage, counting white corpuscles over the programmed duration with simultaneous monitoring of probe voltage and pressure, and acquisition of the hemoglobin value. The electro-valve EV16 is operated in order to restore atmospheric pressure and the motor M1 is actuated in order to take a maximum quantity of air 34.

The electro-valve EV16 is turned off, the electro valves EV10, EV12 and EV1 are operated, the motor M1 is actuated in order to expel the liquid through the drainage outlet 35 and the electro-valve EV1 is turned off.

It will be apparent to those skilled in the art that modifications may be made to the description set forth above without departing from the invention. The scope of the invention is to be limited only by the claims that follow.

What is claimed is:

1. A compact apparatus for analyzing a blood sample having platelets, red corpuscles, white corpuscles and hemoglobin, said apparatus comprising:
    means for pumping comprising:
        a first pump selectively connected to an air source;
        a second pump selectively connected to a lysis reagent source;
        a third pump selectively connected to a diluent source and a water source; and
        a fourth pump selectively connected to said diluent source and said water source;
    means for measuring connected to a transflux source, said first pump, said second pump, said lysis reagent source, and said air source, said means for measuring comprising:
        a measuring chamber fluidically connected to said lysis reagent source, said second pump, said air source, and said transflux source; and
        means for counting said platelets, said red corpuscles, said white corpuscles, and said hemoglobin of said blood sample, said means for counting connected to said measuring chamber for communicating therewith;
    means for dilution connected to said third pump, said fourth pump, said diluent source, said water source, and said measuring chamber, said means for dilution comprising:
        a plurality of containers fluidicially connected to said measuring chamber; and
        a sampling needle selectively connected to said diluent source, said water source, said third pump, and said fourth pump, said sampling needle operating to draw and discharge fluid; and
    valve means for regulating fluid flow between said pumping means, said measuring means, and said dilution means;
    whereby said pumping means, said measuring means, and said dilution means are each arranged as an individual unit thereby permitting compact design of said apparatus.

2. The apparatus according to claim 1, wherein said plurality of containers comprise a waste container, a white corpuscle dilution container, and a red corpuscle dilution container.

3. The apparatus according to claim 2, wherein said means for dilution comprises means for engaging said sampling needle with each of said waste container, said white corpuscle dilution container and said red corpuscle dilution container.

4. The apparatus according to claim 3, wherein said means for engaging said sampling needle comprises a motor adapted to translate said waste container, said white corpuscle dilution container, and said red corpuscle dilution container.

5. The apparatus according to claim 1, wherein said means for measuring measures both said red corpuscles and said white corpuscles in said measuring chamber.

6. The apparatus according to claim 1, wherein said valve means for regulating fluid flow comprises a plurality of electro-valves.

7. The apparatus according to claim 6, wherein one of said plurality of electro-valves is disposed between said diluent source and said water source to selectively close either source, whereby said apparatus is rinsed with water to avoid crystalization.

8. The apparatus according to claim 7 further comprising a plurality of tubes, said plurality of electro-valves connecting said pumps, said sources, said measuring chamber and said plurality of containers, operating to open and close one of said plurality of tubes.

9. The apparatus according to claim 8, wherein said diluent source comprises isotonic diluent, and further wherein said water source comprises distilled water.

10. A compact apparatus for automatically analyzing a blood sample having platelets, red corpuscles, white corpuscles and hemoglobin, said apparatus comprising:
    means for pumping comprising:
        a first pump selectively connected to an air source;
        a second pump selectively connected to a reagent lysis reagent source;
        a third pump selectively connected to a diluent source and a water source; and
        a fourth pump selectively connected to said diluent source and said water source;
    means for measuring connected to a transflux source, said first pump, said second pump, said lysis reagent lysis source, and said air source, said means for measuring comprising:
        a measuring chamber in fluid communication with said lysis reagent source, said second pump, said air source and said transflux source; and means for counting said platelets, said red corpuscles, said white corpuscles, and said hemoglobin of said blood sample, said means for counting connected to said measuring chamber such that both said red corpuscles and said white corpuscles are counted in the same measuring chamber, means for dilution fluidicially connected to said third pump, said fourth pump, said diluent source, said water source, and said measuring chamber, said means for dilution comprising:
  a sampling needle selectively connected to said diluent source, said water source, said third pump and said fourth pump, said sampling needle operating to draw and discharge fluid;
  a plurality of containers fluidically connected to said measuring chamber, said plurality of containers comprising a waste container, a white corpuscle dilution container and a red corpuscle dilution container; and
  means for engaging said sampling needle with each of said waste container, said white corpuscle dilution container and said red corpuscle dilution container; and a plurality of electro-valves adapted to regulate fluid flow between said pumping means, said measuring means and said dilution means;

whereby the said pumping means, said measuring means, and said dilution means are each arranged as an individual unit thereby permitting compact design of said apparatus.

11. The apparatus according to claim 10, wherein said means for engaging said sampling needle comprises a motor adapted to translate said waste container, said white corpuscle dilution container, and said red corpuscle dilution container.

12. The apparatus according to claim 10, wherein one of said plurality of electro-valves is disposed between said diluent source and said water source to selectively close either source whereby said apparatus is rinsed with water to avoid crystalization.

13. The apparatus according to claim 12 further comprising a plurality of tubes, said plurality of electro-valves connecting said pumps, said sources, said measuring chamber and said plurality of containers, operating to open and close one of said plurality of tubes.

14. The apparatus according to claim 13, wherein said diluent source comprises isotonic diluent, and further wherein said water source comprises distilled water.

15. A compact apparatus for automatically analyzing a blood sample having platelets, red corpuscles, white corpuscles and hemoglobin, said apparatus comprising:
  means for pumping comprising:
    a first pump driven by a first motor, said first pump being selectively connected to an air source;
    a second pump actuated by a second motor, said second pump being selectively connected to a lysis reagent source;
    a third pump actuated by said second motor, said third pump being selectively connected to an isotonic diluent source and a distilled water source; and
    a fourth pump actuated by said second motor, said fourth pump being selectively connected to said isotonic diluent source and said distilled water source;
  means for measuring connected to a transflux source, said first pump, said second pump, said lysis reagent source, and said air source, said means for measuring comprising:
    a measuring chamber fluidicially connected to said lysis reagent source, said second pump, said air source and said transflux source; and
    means for counting said platelets, said red corpuscles, said white corpuscles, and said hemoglobin of said blood sample, said means for counting being connected to said measuring chamber such that both said red corpuscles and said white corpuscles are counted in the same measuring chamber;
  means for dilution connected to said third pump, said fourth pump, said isotonic diluent source, said distilled water source, and said measuring chamber, said means for dilution comprising:
    a sampling needle selectively connected to said isotonic diluent source, said distilled water source, said third pump and said fourth pump, said sampling needle operating to draw and discharge fluid;
    a plurality of containers fluidicially connected to said measuring chamber, said plurality of containers comprising a waste container, a white corpuscle dilution container, and a red corpuscle dilution container; and
    a third motor which translates said waste container, said white corpuscle dilution container, and said red corpuscle dilution container into engagement with said sampling needle;
  a plurality of tubes connecting said pumps, said sources, said measuring chamber and said plurality of containers; and
  a plurality of electro-valves operating to open and close said plurality of tubes thereby regulating fluid flow between said pumping means, said measuring means and said dilution means, one of said plurality of electro-valves being disposed between said isotonic diluent source and said distilled water source to selectively close either source such that said apparatus is rinsed with said distilled water to avoid crystalization;
  whereby constituting said pumping means, said measuring means, and said dilution means are each arranged as an individual unit thereby permitting compact design of said apparatus.

16. An automatic hematologic analyzing device comprising:
  a blood sampling device comprising a tube receiving portion and a sampling needle driven by a motor for movement with respect to said tube receiving portion;
  a first, a second and a third container arranged for relative movement with respect to said sampling needle whereby said sampling needle operates to inject fluid in each of said containers, said containers being selectively intended for waste material, white blood cell dilution, and red blood cell dilution, said sampling needle and said containers being in a first assembly together;
  a first, a second and a third pump driven by a common motor, said first pump being connected to said sampling needle for aspiration of a sample of blood by said sampling needle, said second pump being connected via valves to a diluent source and to said sampling device, said third pump being connected via valves to a lysis reagent source and to said sampling device;
  a second assembly comprising a measuring chamber connected via valves to said first, second and third containers; and
  an air pump driven by a motor whereby said air pump operates said second assembly via valves, said air pump and said first, second and third pumps being in a third assembly together.

17. A method for automatically analyzing a blood sample having platelets, red corpuscles, white corpuscles and hemoglobin, said method comprising the steps of:

providing a set of three pumps respectively connected to a sampling needle, a diluent source and a lysis reagent source;

controlling a set of valves disposed between said set of three pumps and said sampling needle, said diluent source and said lysis reagent source such that a blood sample in a sample tube is drawn into said sampling needle;

providing a set of three containers comprising a waste container, a white corpuscle dilution container and a red corpuscle dilution container, said set of three containers each being able to selectively translate into engagement with said sampling needle;

engaging said waste container with said sampling needle; controlling said set of valves to rinse said sampling needle in said waste container;

providing a sample of pre-diluted blood comprising the steps of:
engaging said white corpuscle dilution container with said sampling needle; and
controlling said set of valves, said set of three pumps and said sampling needle to dispense said blood sample and a diluent from said diluent source into said white corpuscle dilution container so as to produce said pre-diluted blood;

providing a sample of twice diluted blood comprising the steps of:
controlling said set of valves, said set of three pumps and said sampling needle so as to draw a sample of said pre-diluted blood from said white corpuscle dilution container into said sampling needle;
engaging said red corpuscle dilution container with said sampling needle; and
controlling said set of valves, said set of three pumps and said sampling needle to dispense said pre-diluted blood and a diluent from said diluent source into said red corpuscle dilution container so as to produce said twice diluted blood;

analyzing said twice diluted blood comprising the steps of:
providing a measuring chamber fluidicially connected to each of said three containers; providing an air pump connected to said measuring chamber;
controlling said set of valves and said air pump such that said twice diluted blood is aspirated from said red corpuscle dilution container into said measuring chamber; and
counting red corpuscles in said twice diluted blood, draining said twice diluted blood and rinsing said measuring chamber; and analyzing said pre-diluted blood comprising the steps of:
controlling said set of valves and said air pump such that said pre-diluted blood is aspirated from said white corpuscle dilution container into said measuring chamber; and
counting said white corpuscles in said pre-diluted blood, draining said pre-diluted blood and rinsing said measuring chamber.

18. The method according to claim 17 further comprising the steps of:

providing a source of water connected to at least one of said three pumps and said sampling needle;

disposing at least one of said set of valves between said water source and said diluent source;

controlling said at least one set of valves to shut off said diluent source and open said water source whereby said rinsing steps are performed using water to avoid crystallization.

* * * * *

UNITED STATES PATENT AND TRADEMARK OFFICE
CERTIFICATE OF CORRECTION

PATENT NO. : 6,555,065 B1
DATED : April 29, 2003
INVENTOR(S) : Francois Melet

It is certified that error appears in the above-identified patent and that said Letters Patent is hereby corrected as shown below:

<u>Title page, Item [54] and Column 1, line 2,</u>
Title, kindly delete "ANALYSING" and add -- ANALYZING --.

<u>Column 1,</u>
Lines 40-41, kindly delete "EP 0 508 495 and EP 0 335 789 whose descriptions are", and insert -- which is --.

<u>Column 6,</u>
Line 55, kindly delete "reagent".
Line 62, kindly delete the second occurrence of "lysis".

<u>Column 7,</u>
Line 6, at the end of the line, kindly delete "," and add -- ; --.
Line 12, kindly delete ",said" and add -- said --.
Line 26, kindly delete "the".
Line 12, kindly insert -- , -- after "source".

<u>Column 8,</u>
Line 38, Line 26, kindly delete "constituting".

Signed and Sealed this

Twentieth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,555,065 B1
DATED : April 29, 2003
INVENTOR(S) : Francois Melet

It is certified that error appears in the above-identified patent and that said Letters Patent is hereby corrected as shown below:

Title page, Item [54] and Column 1, line 2,
Title, kindly delete "ANALYSING" and add -- ANALYZING --.

Column 1,
Lines 40-41, kindly delete "EP 0 508 495 and EP 0 335 789 whose descriptions are", and insert -- which is --.

Column 6,
Line 55, kindly delete "reagent".
Line 62, kindly delete the second occurrence of "lysis".

Column 7,
Line 6, at the end of the line, kindly delete "," and add -- ; --.
Line 12, kindly delete ",said" and add -- said --.
Line 26, kindly delete "the".
Line 12, kindly insert -- , -- after "source".

Column 8,
Line 38, kindly delete "constituting".

This certificate supersedes Certificate of Correction issued July 20, 2004.

Signed and Sealed this

Twenty-eighth Day of September, 2004

JON W. DUDAS
*Director of the United States Patent and Trademark Office*